United States Patent
Wells

[11] Patent Number: 5,862,801
[45] Date of Patent: Jan. 26, 1999

[54] ENDOTRACHEAL TUBE PROTECTOR

[75] Inventor: Sonja Wells, 14880 Hopewell Rd., Alpharetta, Ga. 30201

[73] Assignee: Sonja Wells, Alpharetta, Ga.

[21] Appl. No.: 728,753

[22] Filed: Oct. 11, 1996

[51] Int. Cl.$^6$ ................................................ A61M 16/04
[52] U.S. Cl. ..................................................... 128/200.26
[58] Field of Search ........................ 128/207.17, 207.14, 128/911, 912, DIG. 26, 200.26

[56] References Cited

U.S. PATENT DOCUMENTS

| | | | |
|---|---|---|---|
| 3,946,742 | 3/1976 | Eross | 128/351 |
| 4,167,946 | 9/1979 | Sandstrom | 128/351 |
| 4,344,428 | 8/1982 | Sherman | 128/207.14 |
| 4,351,331 | 9/1982 | Gereg | 128/207.17 |
| 4,527,559 | 7/1985 | Roxburg et al. | 128/207.17 |
| 4,640,273 | 2/1987 | Greene et al. | 128/207.14 |
| 4,896,667 | 1/1990 | Magnuson et al. | 128/207.14 |
| 5,009,227 | 4/1991 | Nieuwstad | 128/207.17 |
| 5,069,206 | 12/1991 | Crosbie | 128/207.17 |
| 5,513,633 | 5/1996 | Islava | 128/207.14 |
| 5,524,642 | 6/1996 | Rosenblatt | 128/849 |
| 5,653,232 | 8/1997 | Rogers et al. | 128/207.17 |

Primary Examiner—John G. Weiss
Attorney, Agent, or Firm—Wood, Herron & Evans, LLP

[57] ABSTRACT

This invention is directed to an endotracheal tube protector and a method of protecting an endotracheal tube. In a preferred embodiment, the endotracheal tube protector includes a first endotracheal tube protector portion and second endotracheal tube protector portion, with each of the portions having an inner surface and an outer surface. The protector further includes a pressure sensitive adhesive layer coated onto the inner surfaces for easily attaching the protector to the tube. Preferably, the first endotracheal tube protector portion is connected to the second endotracheal tube protector portion by a living hinge, which facilitates attachment of the protector to the tube. Preferably, the endotracheal tube protector further includes a soft, compressible cover material attached to the outer surface of each of the first and second endotracheal tube protector portions, which assists in cushioning the patient's teeth and gums when the patient bites down on the protector. In another embodiment, the endotracheal tube protector includes a body having an opening for surrounding at least a portion of the circumference of an endotracheal tube, with the opening having an inner surface coated with an adhesive. The body further includes a pair of opposed free side regions.

15 Claims, 1 Drawing Sheet

ENDOTRACHEAL TUBE PROTECTOR

BACKGROUND OF THE INVENTION

This invention relates to devices and methods used to protect an endotracheal tube and, more particularly, to devices and methods used to protect an oral endotracheal tube.

Endotracheal tubes are used in several different medical situations in order to provide and maintain a clear passageway for air and/or medication to and from the lungs. Depending upon the particular type of endotracheal tube used, this passageway may be created by inserting the tube through the mouth, through the nose or through a tracheostomy incision in the front of the neck and trachea.

When an oral endotracheal tube is used, it is advantageous to protect the portion of the tube which may contact the patient's teeth or gums. Because endotracheal tubes generally are made of a relatively pliant material, a patient may bite down on an oral endotracheal tube so that the lumen or passage through the tube becomes partially or totally constricted. In order to prevent the patient from constricting the endotracheal tube in this fashion, several different endotracheal tube devices have been proposed.

In U.S. Pat. No. 4,896,667, Magnuson et al. disclose an endotracheal tube bite block including an elongated hard core having a generally C-shaped cross-section, which is partially covered on the exterior surface with a softer material, leaving a portion of the hard core exposed. The bite block may be secured to an endotracheal tube by taping the exposed portion of the hard core to the tube. Although the bite block assists in protecting the endotracheal tube in the patient's mouth, the bite block has certain limitations. The bite block is installed on the endotracheal tube by threading an end of the endotracheal tube into and through the hollow opening of the bite block, and sliding the bite block down the endotracheal tube until the block is in the desired position. Because the bite block fits quite tightly on the endotracheal tube, it may be awkward to slide the bite block into position on the tube, particularly once the tube has been inserted into a patient. In addition, in order to ensure positive attachment of the bite block to the tube, the exposed portion of the hard core should be secured to the endotracheal tube with adhesive tape, which requires additional time and material.

In U.S. Pat. No. 3,946,942, Eross discloses an endotracheal tube holder which includes a rigid, protective tube retainer or bite member, which is supported on an arm connected by a friction pivot to a base or chin mount. Although the bite member assists in protecting the endotracheal tube, in order to secure the tube to the bite member, one must secure an elastic tube-retaining strap around the tube and bite member, and even then, the tube may slide within the holder.

In U.S. Pat. No. 4,351,331, Gereg discloses an endotracheal tube holder and bite block for use with an endotracheal tube. However, the device is quite large and cumbersome. In order to install the device on an endotracheal tube, a user must overlap two locking members on one side of the holder assembly and apply a force to the top and bottom portions of the holder assembly on the same side, thereby enabling the bite block to open up enough to slide an endotracheal tube through an opening in the side of the bite block and into the main opening or hole in the bite block.

In addition, in U.S. Pat. No. 4,167,946, Sandstrom discloses a device which may be used to protect a patient's teeth and a medical instrument, such as a tube or probe. The device itself includes a teeth shield member of semi-rigid material and a support member. The support member is in the shape of a slit-open tube in which the instrument, such as a tube, may be inserted radially after the introduction of the instrument into the patient. Although this device may be of value in protecting an endotracheal tube, the device must be tied to the tube by a band, which may be awkward or time-consuming, and even then, the tube may slide within the support member. Also, the teeth-shield member is quite large.

Therefore, it would be desirable to have a device for protecting an endotracheal tube which may be quickly and easily secured to an endotracheal tube without having to use additional ties, tape or fasteners, and without having to thread the device onto a free end of a tube. It also would be advantageous for the same device to provide protection to the patient's teeth and gums, while remaining relatively compact.

SUMMARY OF THE INVENTION

This invention is directed to an endotracheal tube protector and method of protecting an endotracheal tube. In one embodiment, the endotracheal tube protector includes a first endotracheal tube protector portion and a second endotracheal tube protector portion, with each of the portions having an inner surface and an outer surface. The protector further includes a pressure sensitive adhesive layer coated onto the inner surfaces. This endotracheal tube protector is capable of covering and adhering to a selected portion of an endotracheal tube, thereby preventing the portion of the tube from being closed by a normal biting force exerted by a patient biting down on the endotracheal tube protector.

Preferably, the first endotracheal tube protector portion is connected to the second endotracheal tube protector portion by a living hinge. In one embodiment, the first endotracheal tube protector portion and the second endotracheal tube protector portion are formed of a single unitary piece of material, for example, plastic. Alternatively, the first and second endotracheal tube protector portions may be formed of two separate pieces of material. Preferably, the endotracheal tube protector further includes a soft, compressible cover material attached to the outer surface of each of the first and second endotracheal tube protector portions. This cover material assists in cushioning any age patient's teeth and/or gums when the patient bites down on the protector. The cover material itself may be made of any suitable material, for example, rubber, polyurethane, silicone gel or the like.

In another embodiment, the endotracheal tube protector includes a body having an opening for surrounding at least a portion of the circumference of an endotracheal tube, with the opening having an inner surface and the body further including a pair of opposed free side regions. The endotracheal tube protector also includes an adhesive disposed on at least a portion of the inner surface, with the adhesive capable of attaching the endotracheal tube protector to the endotracheal tube. Preferably, this adhesive is a pressure sensitive adhesive.

The method of protecting an endotracheal tube includes attaching the inventive endotracheal tube protector discussed briefly above to an endotracheal tube.

The endotracheal tube and method discussed briefly above provide several benefits and advantages over existing devices and methods. For example, because the protector uses an adhesive, the device may be secured to a tube easily and quickly, without the use of cumbersome tape, ties, straps or the like. And because the adhesive is already coated onto the protector, a clinician may attach the protector in a single step.

In addition, the protector may be attached to an endotracheal tube without having to slip the protector over an end and down the tube into position. Furthermore, with the embodiment having a living hinge, there is no need to snap the device onto the tube; instead, the tube may be surrounded by the two protector portions, and the portions may be pressed against the walls of the tube. Also, in addition to the above-mentioned advantages, the protector incorporates a soft cover material to protect the patient's teeth and gums, while remaining relatively compact.

These and other benefits and advantages will be readily apparent to one of ordinary skill in the art upon reviewing the drawings and detailed description of the invention.

DETAILED DESCRIPTION OF THE INVENTION

Figure 1:
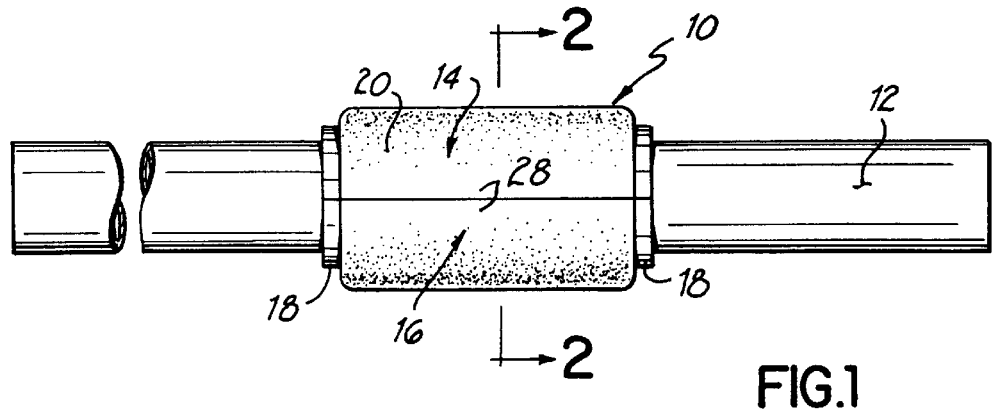
FIG. 1 is an elevational view of an embodiment of the endotracheal tube protector of the present invention, encompassing a portion of an endotracheal tube.
Figure 2:
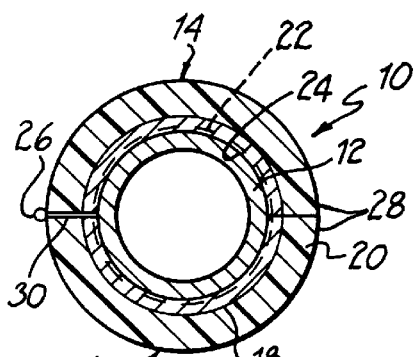
FIG. 2 is a cross-sectional view of the endotracheal tube protector and endotracheal tube of FIG. 1 taken along line 2—2 of FIG. 1.

With reference to FIGS. 1 and 2, an endotracheal tube protector 10 according to the principles of the invention is shown attached to an endotracheal tube 12. The endotracheal tube protector 10 includes a first endotracheal tube protector portion 14 and a second endotracheal tube protector portion 16, with each of the portions 14, 16 encompassing approximately one half of the circumference of the endotracheal tube 12. In addition, the outer surface 18 of each of the protector portions 14, 16 is covered with a soft, compressible covering material 20, which assists in cushioning a patient's teeth and gums when the patient bites down on the endotracheal tube protector 10. The protector 10 itself is held in position on the endotracheal tube 12 by a pressure sensitive adhesive 22 which is coated onto a portion of the inner surface 24 of each of the protector portions 14, 16.

Figure 3:
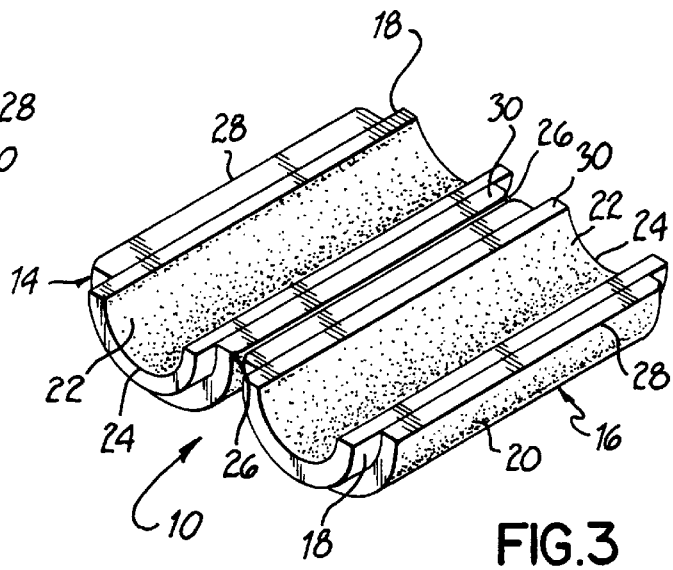
FIG. 3 is a perspective view of an embodiment of the endotracheal tube protector.

As best shown in FIG. 3, each of the endotracheal tube protector portions 14, 16 includes a free side region 28 and a hinge-forming side region 30, with the two opposing hinge-forming side regions 30 being flexibly connected together by a living hinge 26, such as a scored section of material or other similar device. As shown, the first and second endotracheal tube protector portions 14, 16 are formed of a single unitary piece of material, with the living hinge 26 being formed between the hinge-forming side regions 30 of the tube protector portions 14, 16. Alternatively, the endotracheal tube protector portions 14, 16 may be two separate pieces of material, flexibly connected to one another by a living hinge 26, made of a piece of scored plastic material or the like.

Figure 4:
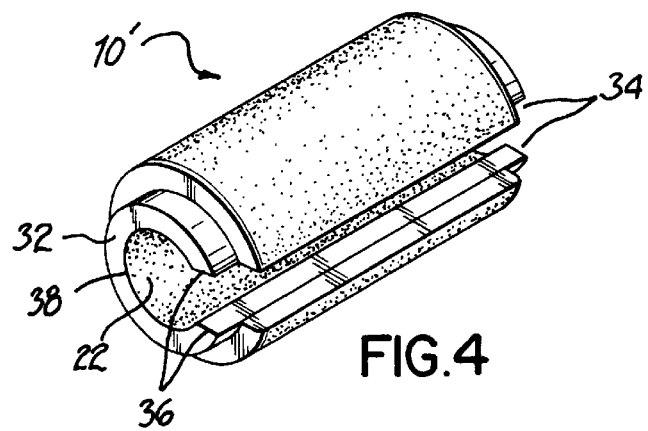
FIG. 4 is a perspective view of another embodiment of the endotracheal tube protector.

With reference to FIG. 4, another embodiment of the endotracheal tube protector 10' is shown having a tubular body 32 which encompasses most of the circumference of an endotracheal tube (not shown). The tubular body 32 includes opposed free side regions 34, each of which has a free side edge 36 which runs along the length of the endotracheal tube protector body 32. Furthermore, each of these edges 36 is sufficiently far apart from the other edge 36 to enable a user to attach the protector 10' onto an endotracheal tube (not shown) simply by aligning the longitudinal axis of the tube with the longitudinal axis of the protector, placing the tube against the opposed free side edges, and bringing each of the free side edges around the tube. The endotracheal tube protector further includes an adhesive 22 which lines the inner surface 38 of the body 32, as well as a soft, compressible cover material 20 covering most of the exterior surface 40 of the body 32.

The endotracheal tube protector of the present invention may be made by injection molding the endotracheal tube protector portions and covering the portions with an adhesive and a soft, resilient, compressible covering material.

As may be seen from the detailed description above, the inventive endotracheal tube protector offers many benefits and advantages over existing devices. For example, because the protector uses an adhesive, the device may be secured to a tube easily and quickly, without the use of cumbersome tape, ties, straps or the like. And because the adhesive is already coated onto the protector, a clinician may attach the protector in a single step.

In addition, the protector may be attached to an endotracheal tube without having to slip the protector over an end and down the tube into position. Furthermore, with the embodiment having a living hinge, there is no need to snap the device onto the tube; instead, the tube may be surrounded by the two protector portions, and the portions may be pressed against the walls of the tube. Also, in addition to the above-mentioned advantages, the protector incorporates a soft cover material to protect the patient's teeth and gums, while remaining relatively compact.

Although the invention has been illustrated by a detailed description of several embodiments, the invention is not limited to these embodiments. Instead, the scope of the invention is to be determined by the following claims and their equivalents.

What is claimed is:

1. An endotracheal tube protector, comprising:
   a first endotracheal tube protector portion and a second endotracheal tube protector portion, each of said portions having an inner surface and an outer surface said inner surface having a configuration adapted to mate with an outer surface of an endotracheal tube; and
   sole means to hold said protector to said tube said means consisting of an adhesive layer coated onto said inner surfaces,
   said endotracheal tube protector adapted to cover and adhere to a portion of an endotracheal tube, thereby preventing the portion of the endotracheal tube from being closed by a normal biting force exerted by a patient biting down on said endotracheal tube protector wherein said outer surfaces are covered with a soft, resilient, compressible material.

2. The endotracheal tube protector of claim 1 wherein said first endotracheal tube protector portion is connected to said second endotracheal tube protector portion by a living hinge.

3. The endotracheal tube protector of claim 1 wherein said first endotracheal tube protector portion and said second endotracheal tube protector portion are two separate pieces.

4. The endotracheal tube protector of claim 1 wherein each of said first and second endotracheal tube protector portions has a cross-sectional curvature which approximates an arc of a circle.

5. The endotracheal tube protector of claim 4 wherein the cross-sectional radius of said first endotracheal tube protector portion is substantially similar to the cross-sectional radius of said second endotracheal tube protector portion.

6. The endotracheal tube protector of claim 5 wherein said endotracheal tube protector further includes a cover material attached to the outer surface of each of said first and second endotracheal tube protector portions, said cover material assisting in cushioning a patient's teeth and/or gums when a patient bites down on said endotracheal tube protector.

7. The endotracheal tube protector of claim 6 wherein said cover material is made of a material selected from the group consisting of rubber, polyurethane, silicone gel and combinations thereof.

8. The endotracheal tube protector of claim 1 in combination with an endotracheal tube wherein said pressure sensitive adhesive on said inner surface is adhered to on outer surface of said endotracheal tube and is the only means holding said protector to said endotracheal tube.

9. An endotracheal tube protector, comprising:
   a body having an opening for surrounding at least a portion of the circumference of an endotracheal tube, said opening having an inner surface, said inner surface being accurate and adapted to mate with an outer surface of an endotracheal tube, said body further having a pair of opposed free side regions; and
   sole means to hold said protector to said tube said means consisting of adhesive disposed on at least a portion of said inner surface, said adhesive capable of attaching said endotracheal tube protector to the endotracheal tube,
   said endotracheal tube protector capable of covering a portion of the endotracheal tube, thereby preventing the portion of the endotracheal tube from being closed by a normal biting force exerted by a patient biting down on said endotracheal tube protector said tube protector having an inner surface and an outer surface comprising a soft compressible material.

10. The endotracheal tube protector of claim 9 wherein said adhesive is a pressure sensitive adhesive.

11. The endotracheal tube protector of claim 10 wherein said body includes:
   a first endotracheal tube protector portion and a second endotracheal tube protector portion, each of said endotracheal tube protector portions having a hinge-forming side region and a free side region; and
   means for flexibly connecting said hinge-forming side region of said first endotracheal tube protector portion to said hinge-forming side region of said second endotracheal tube protector portion.

12. The endotracheal tube protector of claim 11 wherein said means for flexibly connecting each of said portions includes a section of material which is scored, said scored section being flexible.

13. The endotracheal tube protector of claim 11 wherein said endotracheal tube protector encompasses substantially all of the circumference of the endotracheal tube when said endotracheal tube protector is in a closed position.

14. A method of protecting an endotracheal tube, comprising the step of:
   attaching an endotracheal tube protector to an endotracheal tube, said endotracheal tube protector having:
      a first endotracheal tube protector portion and a second endotracheal tube protector portion, each of said endotracheal tube protector portions having an inner surface and an outer surface; and
      a pressure sensitive adhesive layer coated onto said inner surfaces,
   said endotracheal tube protector covering and adhering to a portion of said endotracheal tube, thereby preventing said portion of said endotracheal tube from being closed by a normal biting force exerted by a patient biting down on said endotracheal tube protector wherein general pressure sensitive adhesive is the sole means holding said endotracheal tube protector to said endotracheal tube.

15. A method of protecting an endotracheal tube, comprising the step of:
   attaching an endotracheal tube protector to an endotracheal tube, said endotracheal tube protector having:
      a body having an opening for surrounding at least a portion of the circumference of an endotracheal tube, said opening having an inner surface, said body further having a pair of opposed free side regions; and
      an adhesive disposed on at least a portion of said inner surface, said adhesive capable of attaching said endotracheal tube protector to the endotracheal tube,
   said endotracheal tube protector covering a portion of said endotracheal tube, thereby preventing said portion of said endotracheal tube from being closed by a normal biting force exerted by a patient biting down on said endotracheal tube protector wherein said pressure sensitive adhesive is the sole means of connection said protector to said endotracheal tube.

* * * * *